(12) United States Patent
Glaser et al.

(10) Patent No.: US 7,715,013 B2
(45) Date of Patent: May 11, 2010

(54) OPTICAL SYSTEM FOR PLANT CHARACTERIZATION

(75) Inventors: John A. Glaser, Cincinnati, OH (US); Kenneth Copenhaver, Savoy, IL (US); George May, Stennis Space Center, MS (US)

(73) Assignee: The United States of America as represented by the Administrator of the United States Environmental Protection Agency, Washington, DC (US)

( * ) Notice: Subject to any disclaimer, the term of this patent is extended or adjusted under 35 U.S.C. 154(b) by 513 days.

(21) Appl. No.: 11/520,753

(22) Filed: Sep. 14, 2006

(65) Prior Publication Data
US 2007/0065857 A1 Mar. 22, 2007

Related U.S. Application Data

(60) Provisional application No. 60/717,202, filed on Sep. 16, 2005.

(51) Int. Cl.
*G01N 21/55* (2006.01)
(52) U.S. Cl. .................................... 356/448
(58) Field of Classification Search .................. None
See application file for complete search history.

(56) References Cited

U.S. PATENT DOCUMENTS

| | | | |
|---|---|---|---|
| 3,829,218 A * | 8/1974 | Alyanak | 356/300 |
| 5,072,128 A | 12/1991 | Hayano et al. | |
| 5,412,219 A | 5/1995 | Chappelle et al. | |
| 5,467,271 A | 11/1995 | Abel et al. | |
| 5,625,409 A | 4/1997 | Rosier et al. | |
| 5,764,819 A | 6/1998 | Orr et al. | |
| 5,784,162 A | 7/1998 | Cabib et al. | |
| 5,878,356 A | 3/1999 | Garrot, Jr. et al. | |
| 6,114,683 A * | 9/2000 | Spiering et al. | 250/208.1 |
| 6,160,902 A | 12/2000 | Dickson et al. | |
| 6,366,681 B1 | 4/2002 | Hutchins | |
| 6,567,537 B1 | 5/2003 | Anderson | |
| 6,651,894 B2 | 11/2003 | Nimura et al. | |
| 6,734,973 B1 | 5/2004 | Mutters et al. | |
| 6,813,544 B2 | 11/2004 | Hood et al. | |
| 6,947,144 B2 * | 9/2005 | Kim et al. | 356/417 |
| 7,058,197 B1 * | 6/2006 | McGuire et al. | 382/100 |
| 7,103,481 B2 | 9/2006 | Negri | |
| 7,112,806 B2 * | 9/2006 | Lussier | 250/458.1 |

FOREIGN PATENT DOCUMENTS

WO    WO 2005058018 A2 *  6/2005

* cited by examiner

*Primary Examiner*—Gregory J Toatley, Jr.
*Assistant Examiner*—Juan D Valentin
(74) *Attorney, Agent, or Firm*—Browdy & Neimark PLLC

(57) ABSTRACT

A system is provided to monitor targeted pest populations, disease, presence of transgenic and non-transgenic plants, or targeted pest population in a transgenic crop using remote imagery to discern differences in crops along with pest infestation in all crop varieties. The system relies on the fact that plant leaves are known to change color based on stress, herbivory, and other environmental factors. The system provides a special camera that can see reflected light energy across the visible and near infrared (about 400-1000 nm) to identify these effects.

20 Claims, 9 Drawing Sheets

Detailed example for 307; Supervised analysis (wavelet, neural net, discriminant) performed to separate corn into transgenic or Non-transgenic

Figure 2: RDACSH Hyperspectral Image Collection

205. CCD-array of camera
204. Prism
203. Entrance slit
202. Filter Optics
201. Lens assembly Figure 3: Method 1
Direct identification of plant of genetic history from reflectance Figure 4: Detailed example for 307; Supervised analysis (wavelet, neural net, discriminant) performed to separate corn into transgenic or Non-transgenic Figure 5: Method 2
Indirect identification of transgenic corn from infestation Figure 6. Detailed example for 507; Ratio of reflectance bands Performed to separate corn into infested or non-infested areas Figure 7: Average Reflectance Curves for Corn and Soybean Figure 8: Reflectance Difference for Transgenic and Isolines through Growing Season Figure 9: Reflectance of Transgenic and Non-transgenic Varieties of Corn for 2004 Growing Season

# OPTICAL SYSTEM FOR PLANT CHARACTERIZATION

CROSS-REFERENCE TO RELATED APPLICATIONS

The present application claims priority from provisional application Ser. No. 60/717,202, filed Sep. 16, 2005, the entire contents of which are hereby incorporated by reference.

FIELD OF THE INVENTION

The system relates to monitoring plants and plant groups to distinguish conditions relating to crop characteristics, stress, and pest infestation. The system can also be applied to the assessment of compliance with the required implementation of a non-transgenic crop by growers at a landscape perspective.

BACKGROUND OF THE INVENTION

Sustainable agriculture is a long-term approach that combines efficient production with wise stewardship of the earth's resources. Sustainable agriculture includes developing environmentally benign production techniques. One such method involves the development of transgenic crops that incorporate genes that product toxic gene products, or proteins targeting a specific pest larval form. Incorporating the gene into plants eliminates or vastly reduces the amount of traditional pesticides that must be used on crops. The most serious threat to the efficacy of transgenic plants is the evolution of resistance to expressed toxins by insect pests.

Transgenic plants that produce insecticidal substances, however, should be subject to careful testing to ensure human safety and to minimize adverse environmental impacts. Potential environmental impacts unique to transgenic plants include transfer (by cross-pollination) of the new insecticidal gene to wild or weedy relatives of the transgenic crop, as well as the establishment of self-seeded or vegetative propagated crops such as weed in either managed or natural habitats.

The United States Environmental Protection Agency considers preservation of susceptibility to transgenic toxins to be in the public interest, and proteins such as those produced by *Bacillus thuringienses* are therefore worthy of extra protection (U.S. Environmental Protection Agency and U.S. Department of Agriculture, 1999). Insect resistance management (IRM) relates to practices aimed at reducing the potential for insect pests to become resistant to a pesticide or transgenic plant. IRM is important for transgenic crops, particularly for those crops expressing *Bacillus thuringienses* proteins (commonly called Bt crops), because insect resistance poses a threat to the future use of microbial Bt formulation in organic farming and Bt technology as a whole. Scientists, public interest groups, and organic growers and other farmers have expressed concern that the widespread planting of such genetically modified plants will hasten insect resistance to Bt endotoxins, as well as to other toxins produced by transgenic plants.

Under the Federal Insecticide, Fungicide and Rodenticide Act (FIFRA), the U.S. Environmental Protection Agency requirements for transgenic crop registration are designed to ensure that there will be no unreasonable, adverse effects from the use of a pesticide when economic factors are fully considered. With the application of Bt technology, the EPA has stated that it is working to prevent what would happen if Bt no longer could control insect pests, and more toxic insecticides had to be used in its place. In 2000 the EPA imposed new IRM requirements on registered transgenic crops to combat insect resistance to Bt endotoxins. Sound IRM will prolong the life of transgenic insecticides, and adherence to IRM plans benefits growers, producers, researchers, and consumers.

The U.S. EPA has required seed producers to formulate a program of crop stewardship to include an active crop monitoring program and the adoption of an insect resistance management program as part of registration for transgenic crops that produce an insecticide protein. For example, field corn is a crop in which genes for insecticidal proteins have been inserted to protect against both the European corn borer and the corn rootworm.

The current monitoring program is a shared activity across the industry. This monitoring program is based on sampling for resistant insects during the crop season in four discrete areas that are considered to be potential areas of concern. The insects collected are subjected to a dose-response assay to detect if any of the larvae are resistant to the toxin expressed in the crop plant. The IRM program involves the insecticide protein coupled with a refuge of non-transgenic plant hybrids.

Current EPA resistance management for Bt corn hybrids for European corn borer is 20% of the corn acreage plants to a non-Bt corn hybrid of similar maturity within one half mile of the Bt-corn field. It is recommended that the hybrids be planted at approximately the same date as the transgenic crops. EPA requirements for Bt-corn hybrids for corn rootworm is much the same, with the modification that the refuge must be within the same filed or in an adjacent field. A one half mile distance is not permitted.

The refuge requirement is a legal requirement for companies marketing Bt-corn hybrid. The seed technology companies with the registration are responsible for assuring that framers planting their hybrids meet compliance standards. Failure to meet these standards can result in a company losing its registration or right to sell the hybrids within an area where a significant number of farmers are out of compliance with refuge management regulations.

Although implementation of refuge areas in a resistance management program is a legal requirement, policing the regulation is a formidable task. For this reason, remote sensing technology is considered to be the best method of obtaining a general view of the degree of compliance across large geographic areas and within high adoption areas.

Presently, monitoring of transgenic corn acreage for development of pest resistance rests on the collection of viable pest samples from four specific areas in the U.S. corn belt. There have been concerns that the seed industry is unable to report information about resistance outbreaks in a timely fashion. Since resistance development has been seen to be a "local" phenomenon, the course scale of the sampling used in current monitoring programs could easily miss areas or development of resistance.

The landmass of more than 25 million acres of transgenic corn alone does not permit the level of scrutiny to properly identify resistance development economically at an acre by acre level of inspection.

It is also useful to monitor groups of plants or areas of agricultural or other types of growth for conditions of the plants, such as response to physiological stress, insect infestation, and the like.

SUMMARY OF THE INVENTION

A system is provided to monitor targeted pest populations, disease, physiological conditions, presence of transgenic and non-transgenic plants, or any other plant condition that exhibits a change in reflectance of the plant, over time or as compared to a standard, of incident light. This system uses remote imagery to discern one group of plants from another group of plants, such as to discern transgenic crops from non-transgenic crops, or conditions such as pest infestation or physiological stress in all crop varieties. The system relies on the fact that plant leaves are known to change color based on stress, herbivory, and other environmental factors. The system provides a special camera that can see reflected light energy across the visible and near infrared (about 400-1000 nm) to identify these effects.

The system makes it possible to monitor insect resistance in crops by hyperspectral remote sensing from a platform. That can be airborne, satellite borne, or on a fixed platform, as well as to identify genetically modified crop production in agriculture fields using reflectance captured from an airborne, satellite borne, or platform borne camera system. For the purpose of this application, the term "airborne" refers to systems carried on an aircraft, on a satellite, or on a fixed platform.

Methods are provided for collecting airborne imagery within a given temporal range optimum for the monitoring. This also makes it possible to delineate a crop from other land features using supervised classification techniques.

Insect infestation in a crop can be determined using a spectral ratio in pre-defined portions of the electromagnetic spectrum.

Genetically modified crops can be identified using spectral reflectance using signal processing supervised classification techniques. These techniques can be used to develop maps.

Physiological stress in plants, such as from lack of nutrients, or too little or too much water, can be detected using spectral reflectance using signal processing techniques.

The present system provides a process for identifying genetically modified crops and pest infestation in production agriculture fields using light reflectance captured from an airborne camera system. The process includes collecting the imagery at an optimum temporal range based upon crop phenology. The airborne imagery is geo-rectified to real-world coordinates and calibrated to radiance prior to producing a digital map which indicates the probability that the area contains genetically modified crop or the opposite, and un-modified crop.

A system that can be used to produce remotely sensed digital image data to measure reflectance in plants includes the following:

(a) a digital camera capable of collecting more than 50 frames per second;

(b) an optical filter capable of collecting at least 600 narrow portions of light reflectance from the ground surface at 400 to 1000 nanometers;

(c) a central processing unit for storing and analyzing the date;

(d) algorithms for separating the crop from other land cover features;

(e) algorithms for determining the modification of the crop, genetically or modification by other means; and (f) algorithms for determination of infestation of insects when detecting insect infestation or assaying for genetically modified crops.

The first step in map development is generation of an image via supervised classification techniques which delineate the crop of interest from surrounding land cover. Once the crop of interest is defined, a ratio using pre-defined spectral reflectance areas will be used to delineate areas with the greatest likelihood of condition sought to be detected, such as insect infestation. It is highly likely, in the case of insect infestation, that these areas do not include genetically modified crops, and these areas can be identified for ground crews to visit. Signal processing and classification techniques are combined to specifically delineate genetically modified crops from non-modified crops based on a spectral library of known varietal signatures. This information is then developed into a geographically referenced map for distribution to ground crews for validation of results. Signal processing and classification techniques are combined to identify other types of anomalies or differences in crops, such as physiological stress and the like.

The system provides an analytical method to distinguish crops using hyperspectral imagery.

DETAILED DESCRIPTION

Figure 1:
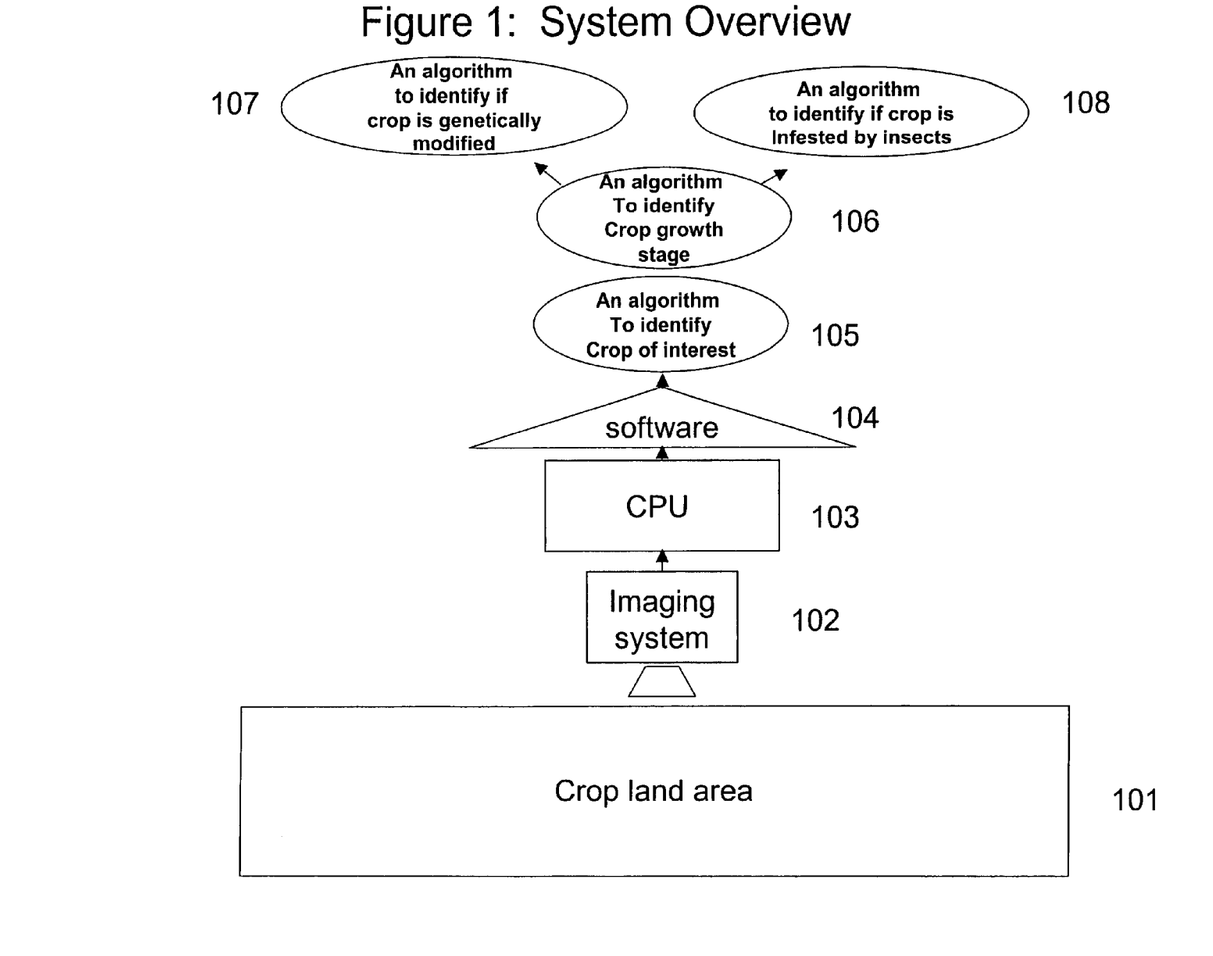
FIG. 1 is a schematic overview of the system.

Referring to FIG. 1, a system overview is shown where the system is used for delineation of the transgenic crops includes collection of imagery from a hyperspectral camera or other multiband imaging device for the collection of multi-band images (102) over a land surface area including, for example, transgenic and non-transgenic crops as well as other land cover features (101). The hyperspectral camera system typically utilizes a central processing unit (103) that can rapidly move data from ram to hard drive storage and store large amounts of data. Software (104) for manipulation of the data after collection is used for image analysis. This software may be configured to convert raw digital values from the camera system to ground referenced, calibrated imagery (104).

The calibrated imagery will give information on reflected solar energy. The calibrated imagery may then be manipulated and analyzed by algorithms to identify physical characteristics such as crop types (105), crop growth stage (106) transgenic crop varieties or genetic composition (107) and crop varieties under insect pressure (108).

The ground parcel (101) the system is imaging will be over a typical agricultural area consisting of agricultural fields of various crop types, trees, streams, homesteads and etc. Imagery will be collected from a small aircraft at an altitude that may be between 1,000 and 12,000 feet as examples or from a satellite platform.

The imaging system (102) is configured to provide a multi-band image such as a hyperspectral or multispectral image. The central processing unit (103) preferably has at least a two gigahertz processor and at least one gigabyte of ram and a 500 gigabyte hard drive, for example. Architecture is preferably optimized for single task focus.

The corresponding software (104) typically consists of commercially available image processing software and proprietary software developed at the Institute for Technology Development. Commercially available products may include ERDAS Imagine, RSI ENVI, MatLab and SAS statistical analysis software, for example examples.

An algorithm (105) for analysis to identify crop of interest is preferably a supervised mahalanobis distance classification, for example, using target signatures developed from research findings. In other words, an algorithm for analysis to identify crop of interest may be a supervised mahalanobis distance classification for example using a reference multi-band image developed from research findings.

An example of an algorithm (106) for analysis to identify growth stage includes a supervised maximum likelihood classification using target signatures for crop growth stage developed during previous research. In other words, an algorithm for analysis to identify growth stage may include a supervised maximum likelihood classification for example using a reference multi-band image for crop growth stage developed during previous research.

Figure 3:
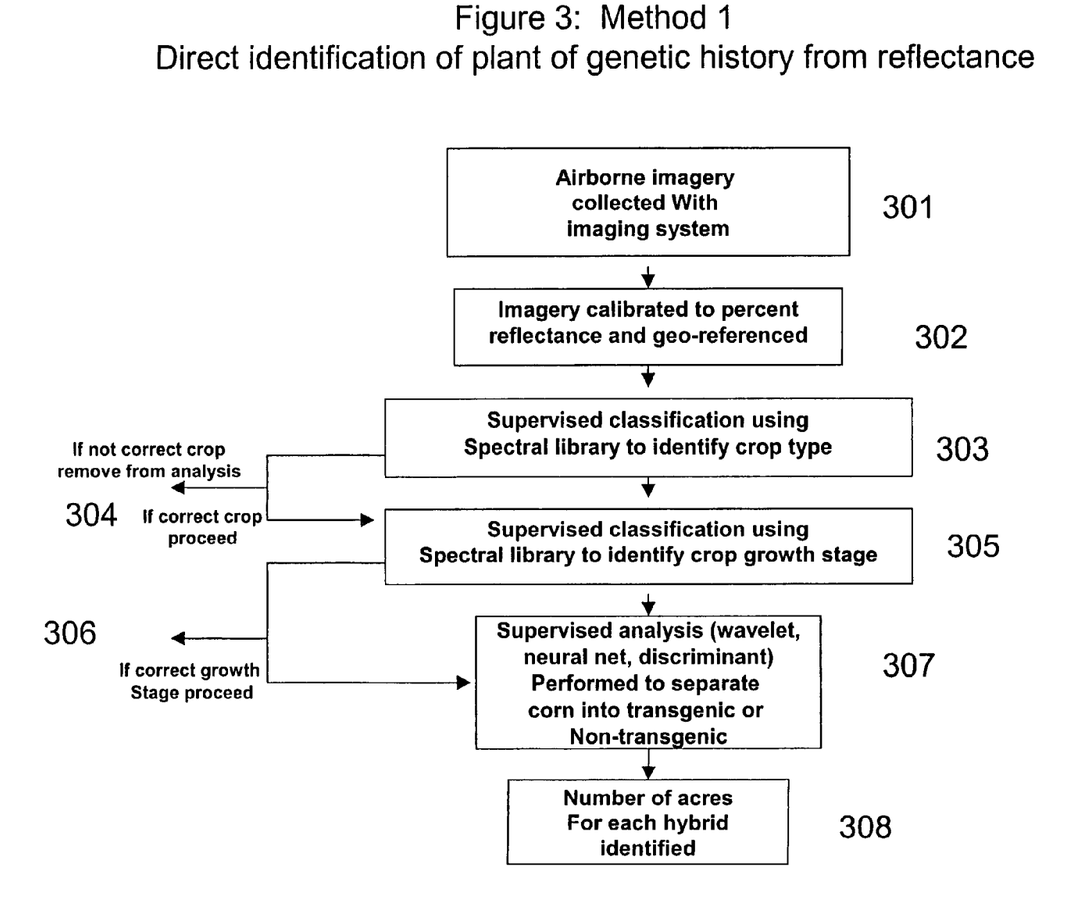
FIG. 3 is a schematic of direct identification of transgenic hybrid plants from reflectance information.
Figure 4:
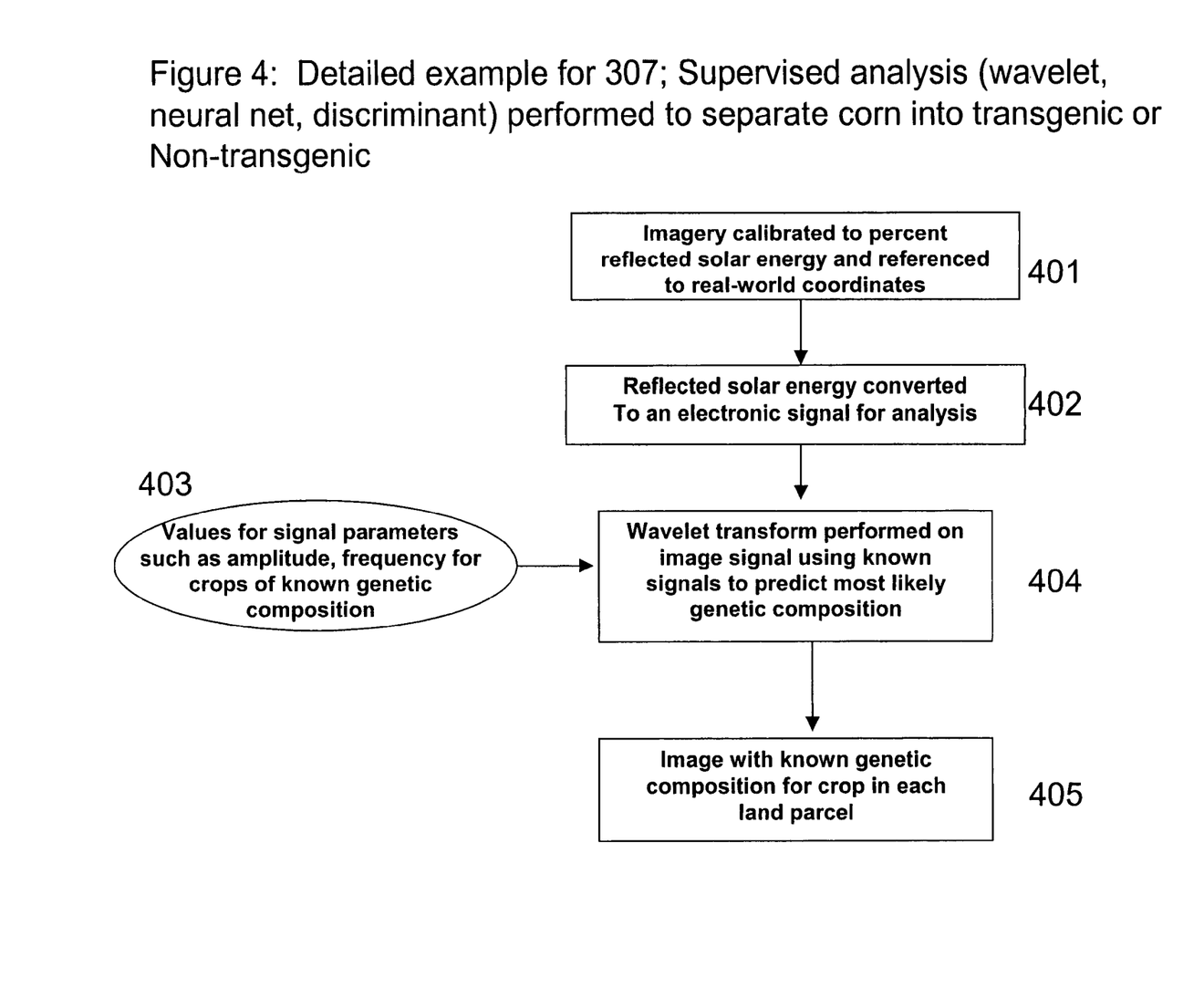
FIG. 4 is a detailed example for 307.

As further discussed below, an example of an algorithm (107) for identification of genetically modified crops or the genetic composition of a crop is shown in FIG. 3, and an example of an algorithm (108) for identification of insect infestation within crops is shown in FIG. 4.

Figure 2:
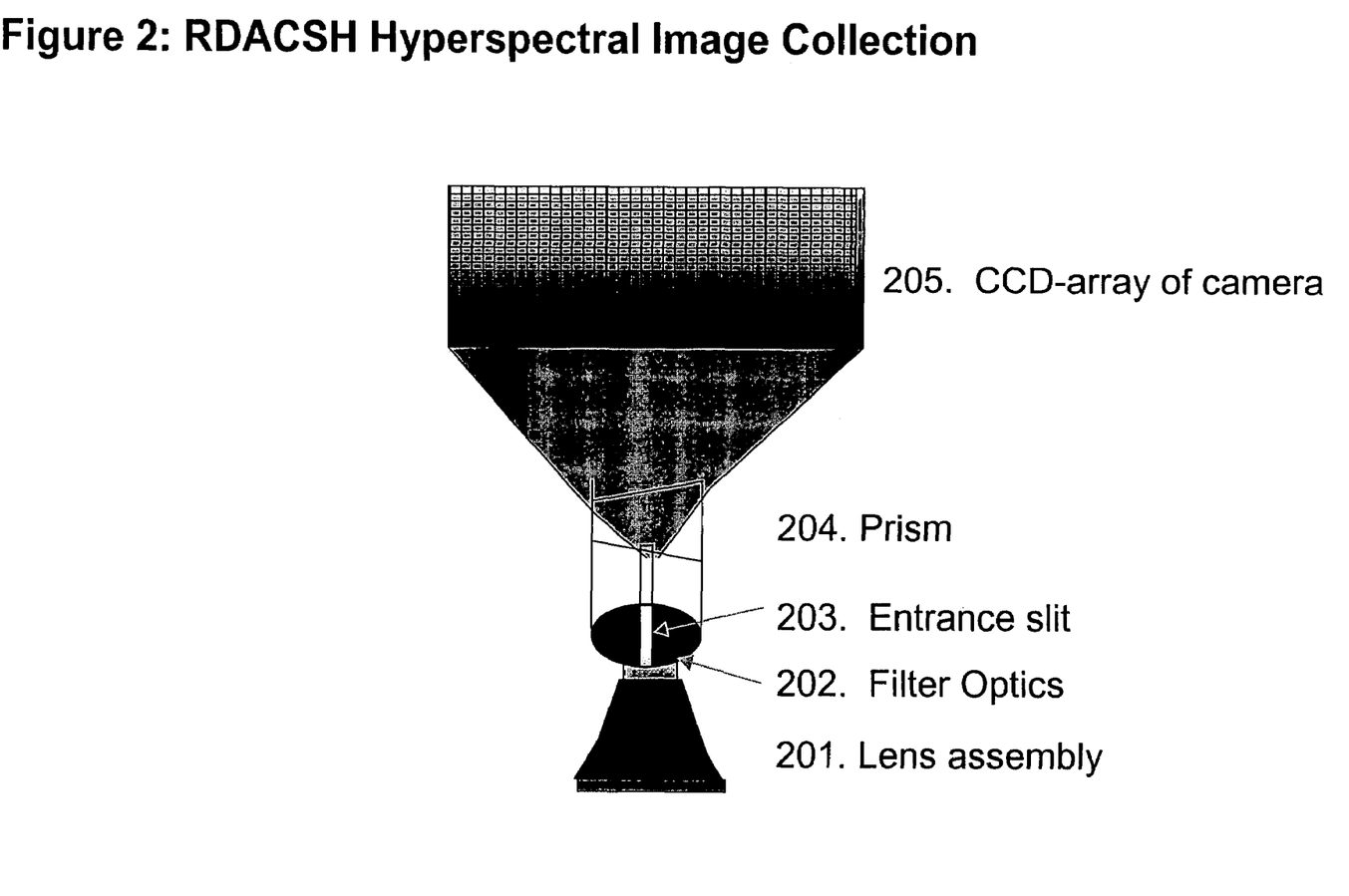
FIG. 2 illustrates RDASCH hyperspectral image collection.

Referring to FIG. 2, an example of an RDACSH Hyperspectral Image Collection systems is shown where the system developed for data collection includes a lens assembly for the correct focus of the reflected solar radiation for a specific parcel of land into the imaging system (201). For example, an industrial quality c-mount lens with near-infrared correction and a 1" or ¾" format could be used.

A prism spectrograph (202 to 204) may also be used to split the reflected solar radiation into distinct wavelengths. This is performed via the entrance of light through a narrow entrance slit which allows a specific portion of reflected solar energy into the spectrograph at any time (202). The reflected solar energy may then be focused using an optical lens (203). Typically, a prism (203) then allows the reflected solar radiation in specific wavelengths to pass based on prism thickness, an additional optical lens is then used to focus the reflected solar energy onto a camera's ccd or cmos array (204).

The same effect of collecting specific wavelengths of reflected solar energy may also be obtained via a liquid crystal tuneable filter which changes the thickness of liquid crystal via a changing electrical charge controllably allowing a specific wavelength at a time to pass based on crystal thickness. Additionally, a light blocking filter which allows light from a specific wavelength or group of wavelengths to pass using color coatings or any other device which can manipulate solar radiation into specific wavelengths, may be included.

In other words, the system is preferably designed to be able to aid in identifying the genetic composition of crops for all crop types, not just transgenic corn or transgenic cotton, for example. A lens (201) may be any suitable lens such as a 1-inch format CCD lens. A grating filter (202) may be included to bend reflectance (i.e. reflected solar energy) into the prism for additional manipulation. A prism (203) may then function to bend reflectance into specific wavelengths, for example. Reflectance may be captured from about 400 to about 1000 nm, at a slit width approximate to the length and width of one cell array on the camera's CCD-array or other sensor device.

Preferably, a CCD-array camera (204) may collect image frames at least 50 times per second, and should have a coverage width appropriate for collection of imagery over a large area, 1,600 pixels, for example. The camera preferably also has a suitable high signal to noise ratio.

Referring to FIG. 3, an algorithm is shown which may be used to convert reflected solar energy from a crop into an information product which will identify whether the crop is a transgenic variety or a non-transgenic variety or identify the crop's genetic composition, growth stage, disease state, infestation, effects from soil deficiencies or dehydration, and other plant condition or health stressors, etc. Research has indicated that the reflectance of a transgenic crop is different from a non-transgenic crop and this difference can be identified using algorithms which cluster the data into groups based on actual reflectance and wavelength, for example, or by treating the reflectance signature as a signal which can be manipulated by signal processing software.

A first method includes direct identification of genetic composition of transgenic hybrids from reflected solar energy. As shown in FIG. 3, high spectral resolution, narrow bandwidth imagery (301) or multi-band imagery may be collected from a system described, for example, in FIG. 2 at a high spatial resolution such as about 0.5 to about 1 meter.

Imagery (302) may be georeferenced, for example, to Universal Transverse Mercator coordinates using on-board inertial and geographic information from a global positioning system/inertial navigation system and calibrated to reflectance based on at sensor radiance values and an atmospheric calibration equation for date of flight, such as, for example, algorithm (303) described above in FIG. 1. If a crop is not crop of interest, then analysis will not be performed on that parcel of land (304). If crop is crop of interest than additional analysis will be performed, such as by, for example, algorithm (106) described above in FIG. 1.

If crop is defined as being in appropriate growth stage for a transgenic or genetic composition delineation algorithm to function at peak performance than analysis will continue (306). If crop not at this growth stage than analysis stops.

A supervised analysis, for example includes, a wavelet, a neural network or discriminate analysis may be performed on the land parcels identified as appropriate crop at appropriate growth stage preferably using target signatures developed during previous research (307). Algorithm 307 is described below in FIG. 4. A supervised analysis, for example a wavelet, neural network or discriminant analysis, may be performed on the land parcels identified as appropriate crop at appropriate growth stage using reference multi-band images developed during previous research. Algorithm 307 is discussed below in FIG. 4. Algorithm (308) identifies the number of acres for each hybrid plant identified.

Preferably, each parcel of land (about 0.5 to about 1 meter per pixel, for example) may be identified as appropriate crop and growth stage may then be identified on a map as either a transgenic variety of that crop or a non-transgenic variety of that crop based on a delineation of the genetic composition (309).

Referring to FIG. 4, an example of algorithm or step 307 in FIG. 3 is shown including supervised analysis (wavelet) performed to separate crop into known genetic composition. Imagery or multi-band image should preferably be in same format as origin imagery for original electronic signal parameters mentioned in step 403 (percent reflected solar energy, for example) (401). Reflected solar energy may then be converted to electronic signal (an electronic wave) by off-the-shelf image processing software package such as MatLab (402), for example.

A database containing signal parameters for waves of crops of known genetic composition may then be opened for input (403). Wavelet transform analysis, for example, may then compare the signal parameters for the crop of unknown genetic composition for each land parcel to those in database. Preferably, a best fit routine is then used to determine genetic composition of unknown crop (404). A new image may be created of each land parcel imaged with crop's genetic composition predicted (405).

Figure 5:
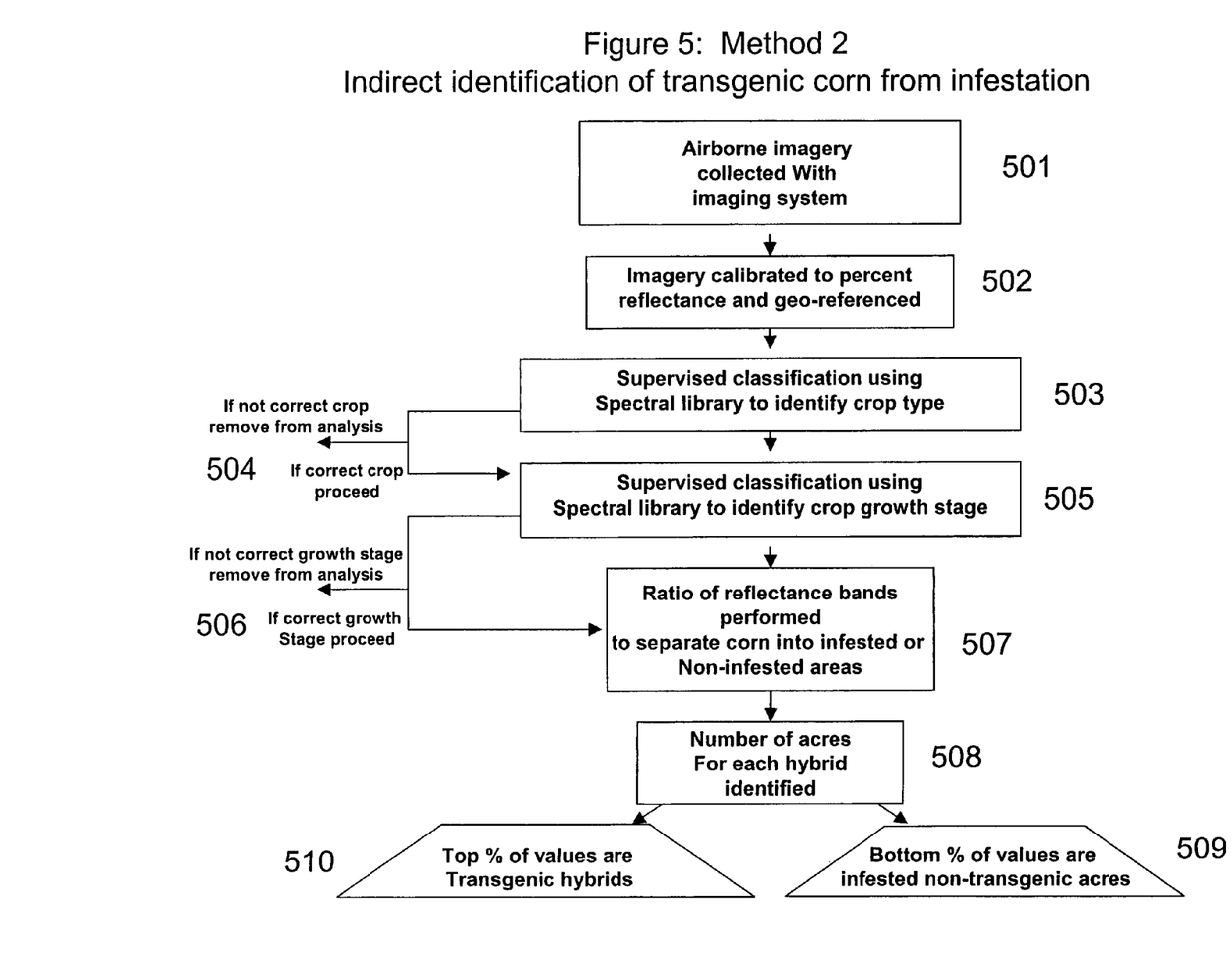
FIG. 5 shows a method for indirect identification of transgenic corn.

Referring to FIG. 5, average reflectance curves for corn and soybean are shown, to illustrate an example of how a crop under stress by insect consumption or pest infestation will reflect solar energy or light differently than a healthy plant. A stressor or health stressor such as pest or insect infestation will typically cause a plant to reflect solar energy differently. This reflectance difference can be identified and amplified by receiving or recording and manipulating imagery of the reflectance. Ratios of reflectance bands (dividing a band or bands at which healthy vegetation reflects more solar energy or sunlight (typically the near-infrared) by a band or bands in which a healthy plant reflects less solar energy or light (typically the green or red) heighten the ability of imagery to identify stressors of plants. Determining times of year and locations of reflectance changes can pinpoint the type of stress, such as insect pressure, for example. Transgenic crops by the very nature of the plant, should not be impacted by insects. Therefore, in some cases, it would be safe to assume a crop identified by imagery as infested by insects is not a transgenic crop.

A second method includes indirect identification of genetic composition or transgenic varieties from insect or pest infestation. High spectral resolution, narrow bandwidth imagery also known as multi-band imagery may be collected by an imaging system (described in FIG. 2, above) at a high spatial resolution, about 0.5 to about 1 meter, for example (501), to aid in such identification.

For example imagery georeferenced to Universal Transverse Mercator coordinates using on-board inertial and geographic information from a global positioning system/inertial navigation system and calibrated to reflectance or reflected solar energy based on at sensor radiance values and an atmospheric calibration equation for date of flight (502) may be used. A supervised classification using a spectral library, for example, to identify a crop type may be used (described above in FIG. 1) (503).

If a crop is not the crop of interest, than analysis will not be performed on that parcel of land. If crop is the crop of interest than additional analysis will be performed, for example, by an algorithm to identify crop stage growth, transgenic, infestation, etc (described above in FIG. 1) (504).

If crop is defined as being in appropriate growth stage for a transgenic or genetic composition delineation algorithm to function at peak performance, then analysis will continue. If the crop not at this growth stage, then analysis stops. Analysis may include a ratio (division) of reflectance or reflected solar energy bands chosen based on research results will be performed, for example, such as at wavelengths at 737 nm and 648 nm.

Each parcel of land (about 0.5 to about 1 meter pixel, for example) identified as appropriate crop and growth stage will then be identified on a map as either a transgenic variety of that crop or a non-transgenic variety of that crop. A percentage of the ratio values may then be identified as transgenic varieties. While another percentage of the ratio values may then be identified as non-transgenic varieties which are very likely infested. For example, the top 10% of values may be chosen as locations with a high likelihood of transgenic corn while the bottom 10% may be chosen as locations with a high likelihood as non-transgenic infested areas. More exact percentages will be based on available agricultural statistics and previous research findings.

Figure 6:
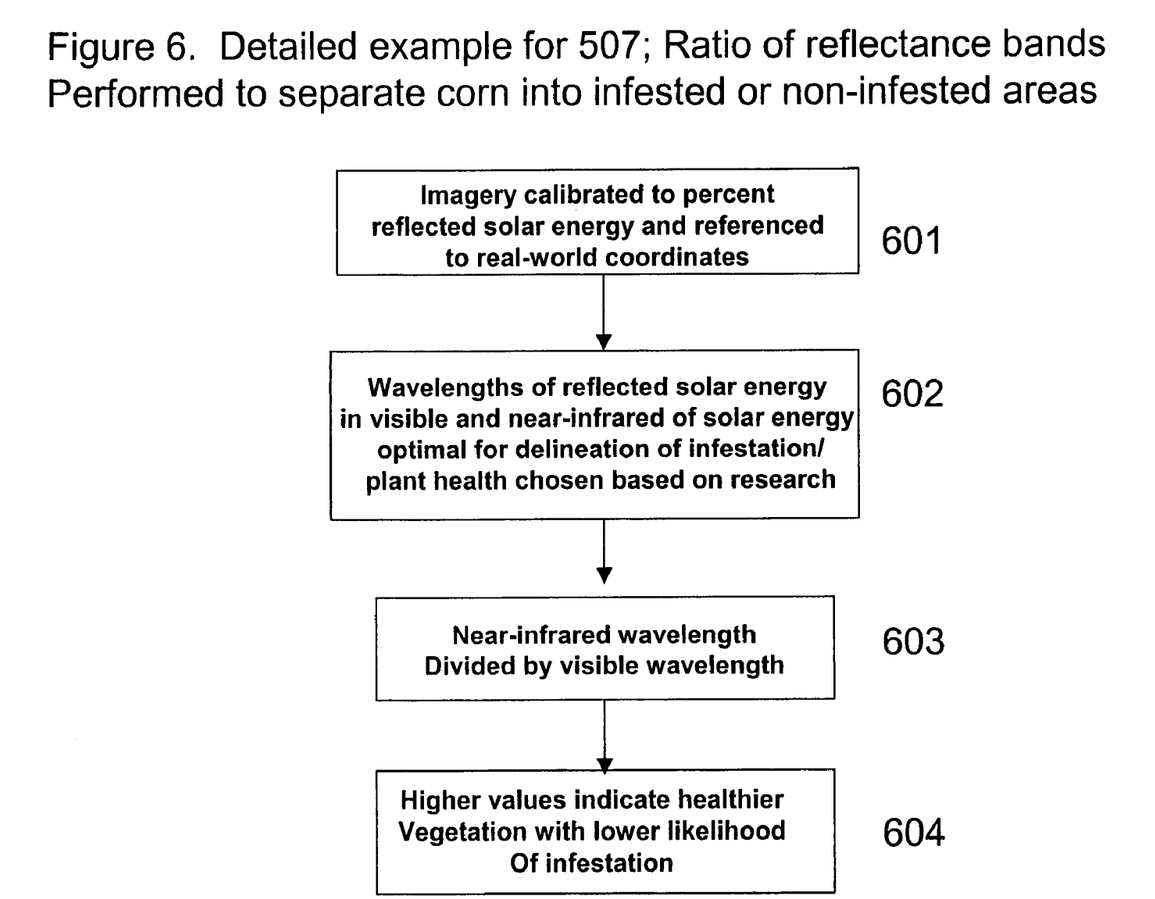
FIG. 6 shows ratios of reflectance bands for infested and non-infested corn.

Referring to FIG. 6, a reflectance difference for transgenic plants and isolines though a growing season for a transgenic and non-transgenic corn are shown, where supervised analysis (wavelet) may be performed to separate crops into known genetic composition. Input imagery is preferably calibrated to ensure reflectance differences for ratio (step 603 discussed below) are valid, with calibration to percent reflected solar energy as a good example (601).

Wavelengths of reflected solar energy which research has indicated are most indicative of stress from insect damage may then be chosen in the near-infrared and visible portions of the spectrum (602). The chosen near-infrared wavelength may then be divided by the chosen visible wavelength (603). The resulting image band may have higher values where healthier or more crop exists and lower values where crop may be infested with insects (604).

Figure 7:
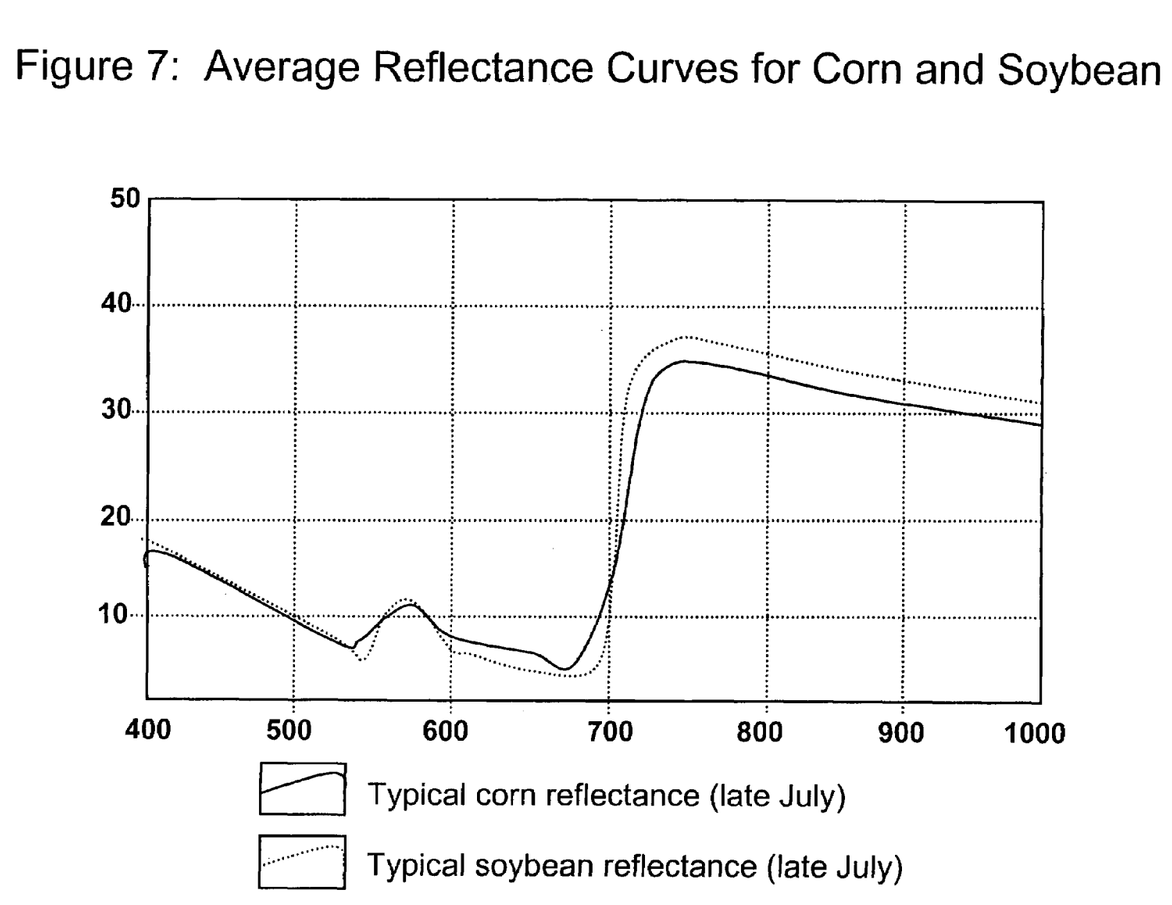
FIG. 7 shows the average reflectance curves for corn and soybeans.

Referring to FIG. 7, an example of average reflectance or reflected solar energy curves for transgenic and non-transgenic varieties of corn are shown. In other words, FIG. 7 is an example of the difference between typical reflectance curves for corn and soybean in late July as an example. The corn at this time of year has tasseled and is placing photosynthetic emphasis on filling in grain while the soybeans are reaching a stage of maximum growth and vigor. The soybeans have a stronger vegetation signature with higher reflectance in the near infrared and green and lower reflectance in the red than the corn.

Figure 8:
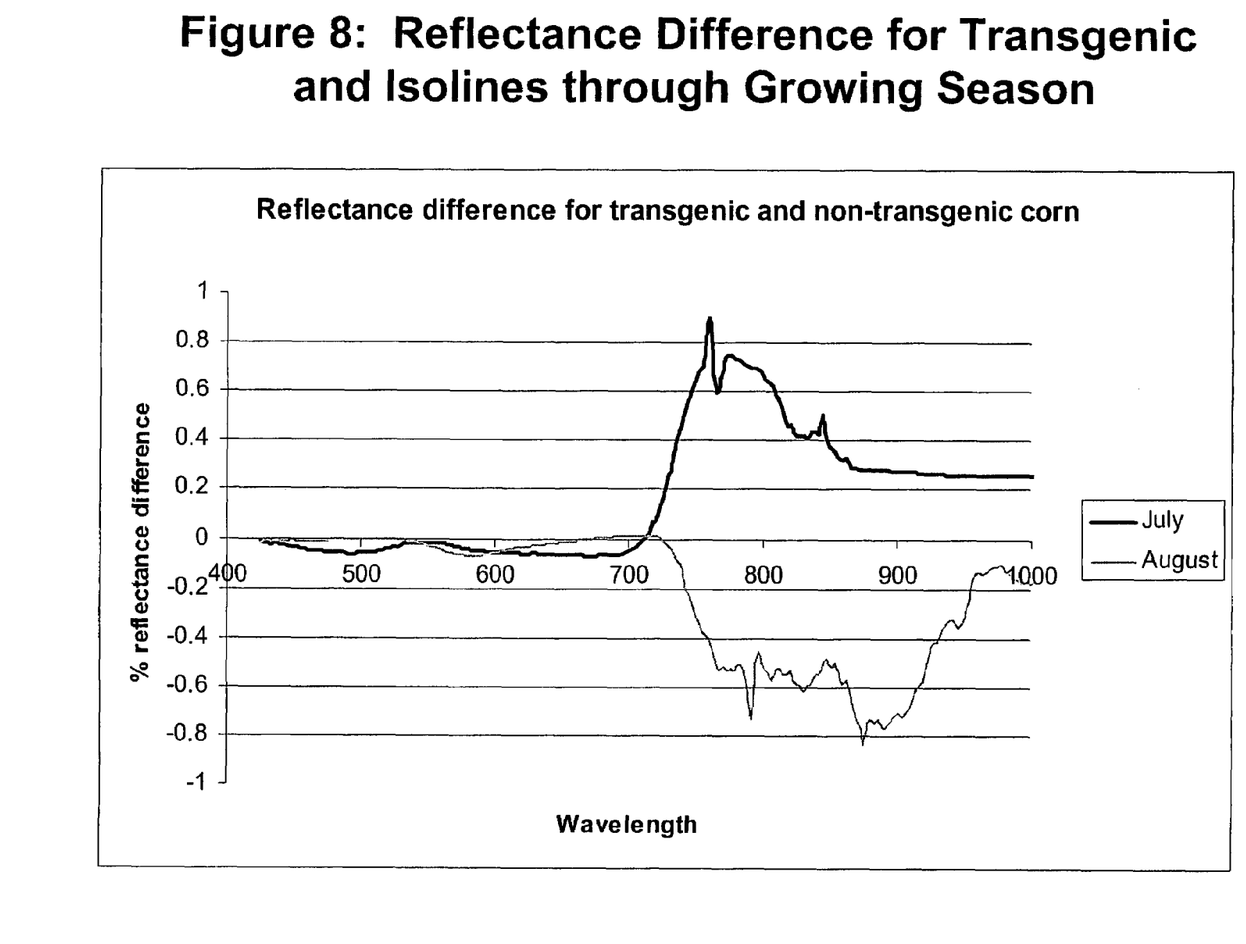
FIG. 8 shows reflectance difference for transgenic and isolines.

Referring to FIG. 8, an example of reflectance difference or difference in reflection of solar energy example for transgenic and isoline varieties of corn throughout a growing season are shown. In other words, FIG. 8 indicates an example of the differences in reflectance found between transgenic varieties of corn and non-transgenic varieties throughout a growing season. This information was derived from imagery collected over plots in 2004 and 2005. The difference is found primarily in the near-infrared and is at a maximum in late August in the northern hemisphere.

Figure 9:
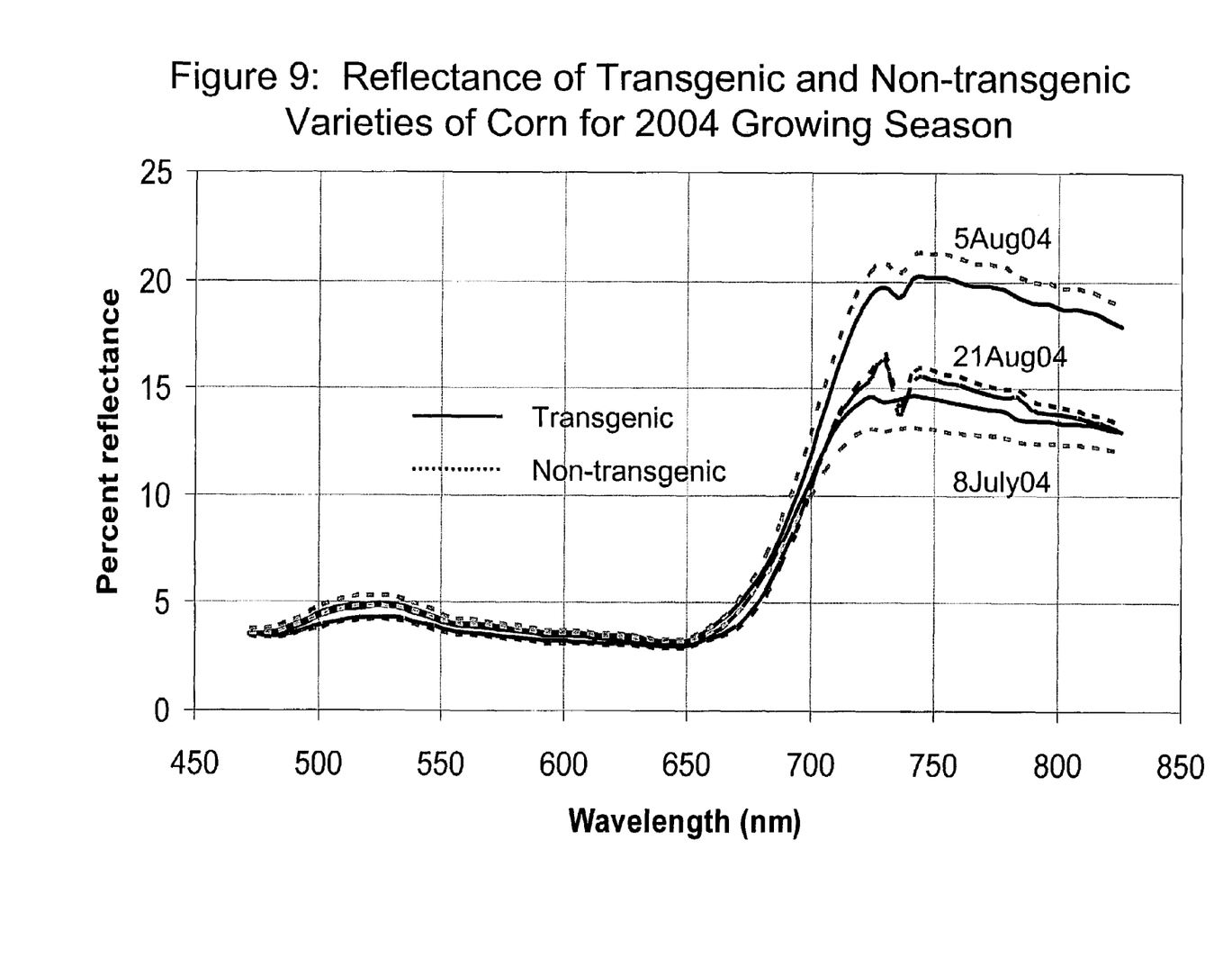
FIG. 9 shows reflectance of transgenic and non-transgenic varieties of corn.

Referring to FIG. 9, an example of reflectance of transgenic and non-transgenic varieties of corn for 2004 growing season is shown. Average reflected solar energy for plants of different genetic composition is seen. In other words, FIG. 9 shows an example of average reflectance for transgenic and non-transgenic corn for two dates in 2004. This imagery was collected over a field in Minnesota. This imagery indicates that non-transgenic varieties have a higher reflectance in the near-infrared, as seen in the early August imagery.

EXPERIMENTAL

Three designed plantings of corn varieties were organized at field settings in Iowa, Nebraska, and Pennsylvania. These plantings were composed of a selected series of corn varieties that included transgenic varieties with their nearest non-transgenic relative. The corn plots were established in 2004 with Bt-expressing and non-transgenic corn hybrids. Each non-transgenic hybrid was selected as a near isoline to the paired Bt hybrid. Each site was organized as a complete factorial of treatments involving the corn hybrids and infestation with European Corn Borer (*Ostrinia nubilalis*). Agronomic practices (irrigation, fertilization etc) at each test plot were recorded and kept comparable. Weather events as recorded by site weather stations and other environmental factors were recorded.

Selected Corn Hybrids

| CrylAb hybrids | | | |
|---|---|---|---|
| NK | N60-B6 | 107d | Bt11 |
| NK | N60-N2 | 107d | near iso |
| DeKalb | DK5B-78 YGCB | 108d | Mon810 |
| DeKalb | DK57-01 | 107d | near iso |
| Pioneer | P34N44 | 110d | Mon810 |
| Pioneer | P34N43 | 110d | near iso |
| CrylF hybrids | | | |
| Pioneer | P34N42 | 111d | Tc1507 |
| Pioneer | P34N43 | 110d | near iso |
| Cryl3Bbl hybrids | | | |
| DeKalb | DKC 60-12 | 110d | Mon863 |
| DeKalb | DKC 60-15 | 110d | near iso |

Random Block Design of Treatments

| Hybrid | Treatments |
|---|---|
| 1. N58-D1 | not infested |
| 2. N58-F4 | not infested |
| 3. P34B98 | not infested |
| 4. P34B97 | not infested |
| 5. DK589Bty | not infested |
| 6. DK585 | not infested |
| 7. DK589Bty | 1$^{st}$ generation ECB |
| 8. DK585 | 1$^{st}$ generation ECB |
| 9. DK585 | 1$^{st}$ generation grits only |
| 10. DK589Bty | 2$^{nd}$ generation ECB |
| 11. DK585 | 2$^{nd}$ generation ECB |
| 12. DK585 | 2$^{nd}$ generation grits only |
| 13. P34M93 | not infested |
| 14. P34M94 | not infested |
| 15. W5524 | not infested |
| 16. W552 | not infested |

Iowa and Pennsylvania: 1-16;
Nebraska: 3-12 irrigated and 3-12 dryland

Remote Imagery Experimental Design

A complete random block design of all treatments was replicated five times. The treatment plots had the dimension of four corn rows by 30 ft. A 30 ft buffer was established between plots set replicates. Treatments included two hand infestations with European Corn Borer larvae. The 1$^{st}$ infestation was accomplished roughly 4 weeks later. Damage to the corn plants was assessed by visual evaluation using the Guthrie rating. Airborne hyperspectral imaging of all plots was conducted on a rotating two-week schedule. A total of 7 imaging were undertaken starting Jun. 22, 2004.

Imagery Experimental Design

Ground Collection

Two sets of gray-scale calibration tarps were laid out on the first date of acquisition for each study site as close as possible to the fields of interest. These tarps varied in their reflectance values (2%, 4%, 8%, 16%, 32%, 48%, 64%, 83%). Radiometer scans were taken for the tarps as close to flight time as possible. The placards are guaranteed by the manufacturer to within +/−1% reflectance but scans ensured proper calibration for the date of the flight. This information provided the necessary standardization of the reflectance from the corn crop.

Data Collection

Airborne hyperspectral imagery was collected from a fixed wing aircraft using the RDACSH hyperspectral sensor (Mao, 2000). Imagery was be acquired for four research sites located in Illinois, Iowa, Pennsylvania and Minnesota at times designated as optimum for the separation of varieties for the delineation of insect infestations/hybrids. The 12-bit RDACSH can collects up to 256 bands of spectral information over the 400 to 1000 nm range. The sensor has a swath of 640 pixels and can collect airborne imagery at a spatial resolution of 0.5 to 2 meter from altitudes of 610 to 3,658 meters. There is a trade-off between spectral and spatial resolution with the RDACSH system. The bottleneck is the amount of data the camera can transport at any given time to the computer. When the camera transports data at a faster rate (higher spatial resolution) than the spectral resolution, then the rate of data acquisition was adjusted to compensate. At the spatial resolution planned for this research (0.5 meter) a spectral resolution of 128 bands were available.

Acquisition of the imagery was conducted by Precision Aviation, an airborne imaging firm with five years experience collecting RDACSH3 imagery. The Precision Aviation plane was outfitted with a gyro-stabilized mount which is required to ensure the geometric quality of the RDACSH3 imagery.

Ground Data Collection

Two sets of gray-scale calibration tarps are laid in the ground near the study area fields during the first date of acquisition. The tarps were left at the study sites and laid out for all future flights if USDA or other personnel are available. These tarps varied in their reflectance values (2%, 4%, 8%, 16%, 32%, 48%, 64, 83%). Radiometer scans are taken for the tarps as close to flight time as possible. The placards are guaranteed by the manufacturer to within +/−1% reflectance but the radiometer scans ensure proper calibration for the date of the flight. Each tarp was 4.572 meters square, giving a tarp to 0.5 meter pixel ratio of 9.144:1. This is above the 8:1 ratio recommended (Moran et al., 1997). Results have indicated the 8:1 ratio will result in at least four pure pixels within each tarp for calibration.

The RDACSH's gain and integration speed are at settings to maximize dynamic range without saturation for any ground features. Regardless, no tarp reflectance above the 48% and below the 8% was used in the calibration equation based on research which has demonstrated that tarps above or below these regions are too affected by other parameters such as surrounding surfaces and atmosphere to be used in the equation (Moran et al., 2001). Often when these tarp reflectance values are included in the equation, the result is no longer linear and may have reflectance values below zero.

Data Processing

The RDACSH3 imagery was first corrected for atmospheric and camera noise. Camera noise correction was performed using equations developed for the systems by the NASA Sensor Calibrating Laboratory at the Stennis Space Center. The noise corrected digital image numbers, permitted comparisons between data obtained from this study and other camera systems with different sensors. This was performed using an empirical line calibration equation between the digital numbers for the calibration tarps retrieved from the imagery and the true reflectance values for each tarp based on the radiometer scans. The imagery also required both rectification and geographic referencing. The RDACSH3 sensor is a line scanner, and thus, each line acquired by the sensor is a separate image with unique distortion caused by the roll, pitch, and yaw of the aircraft. This distortion is especially apparent when caused by the roll of the aircraft. Subtle changes in the look angle of the plane result in major distortion in the imagery. The imagery was first straightened using a simple program that allows the user to draw a line in the image over an area of a linear feature perpendicular to the roll distortion of the image, such as a road or field edge.

Imagery was geo-referenced to field boundaries data and other study area feature data after straightening. The number of ground points required is dependent on the accuracy of the source. If a digital ortho-photo was used then 30 to 40 ground truth points were required. However, if GPS points from a sub-meter accuracy GPS receiver were used to collect geographic coordinates for well-defined features than 20 to 30 points were sufficient. However, with the design in small plots the opportunity does present itself to deploy small fixed targets around and within the plots for geo-rectification. Sixteen 0.5 meter square wooden panels, painted white placed at the corners and between plots and then ground referenced with a centimeter accuracy GPS, were found to develop $1^{st}$ order-polynomial geo-correction equations with less than 0.5 pixel accuracy results when used to geo-reference 0.5 meter resolution hyperspectral imagery.

The noise-corrected digital image numbers were then converted to percent reflectance (Moran et al., 2001). Reflectance values, instead of digital numbers, permitted comparisons. This was performed using an empirical line calibration equation between the digital numbers for the calibration tarps retrieved from the imagery and the true reflectance values for each tarp based on the radiometer scans. Concurrent flights will continue to use tarps.

Preparation of the Imagery Analysis

Areas within fields/plots of transgenic and non-transgenic corn, as well as areas with and without pest infestation, were identified and delineated with a global positioning system on a date approximate to image data acquisition. Areas with the proper spatial resolution (greater than 0.5 meter) for the RDACSH camera systems were emphasized.

Extraction of Reflectance Values for Statistical Analysis

Reflectance values of geo-referenced, calibrated airborne imagery was extracted from known locations of non-transgenic and transgenic corn as well as areas with pest infestation information. This information was saved to ASCII files and tied to ground truth information for statistical analysis. Each plot in the design was 9.144 meters by 3.81 meters. This design would allow for the extraction of approximately 56 pixels per plot including the removal of border pixels. With a designed five replications per treatment 280 reflectance spectra were available for analysis for each treatment.

Index Production and Image Classification

A number of common vegetation indices were generated from imagery and used to attempt to separate the corn varieties and to delineate pest infestation levels. Supervised and un-supervised classification algorithms such as ISODATA (ERDAS Staff, 1997), spectral angle mapper (ENVI Staff, 1997) and the pixel purity index was also be performed to determine if, and to what extent corn varieties and pest levels can be delineated using imagery. Other image processing techniques such as principle components and derivatives analysis were also performed on the image dataset to determine the effectiveness of these techniques. Accuracy assessments were performed on the results of each classification to determine how often the technique was able to accurately place pixels in the correct class.

An error matrix was developed for the accuracy assessment (Congalton, 1991). The error matrix provided information on an overall accuracy for the classification "How many pixels were identified as the correct hybrid/pest infestation level" but also provided information on each individual class with a producer's accuracy (of the ground truth pixels for a particular class how many were correctly identified by the classification) and a user's accuracy (how many ground truth pixels from other classes were wrongly identified as that class by classification). The accuracy required for establishing success for the technology was determined by the decision process of the EPA.

Image Processing and Analysis

The first objective of this research was to determine the degree to which imagery can detect insect damage in transgenic and standard corn varieties. The test for this was an analysis of variance to determine if there is separability in the reflectance of corn with different levels of pest infestation as determined by ground truth information collected in the study site fields. The variables in this situation were reflectance in each band of imagery or the value for various vegetation indices. The test condition was the level of infestation as derived from ground truth. This could be quantified by the number of pests present, condition of the corn or degree of evidence of pest damage to the corn. In the ANOVA indicates significant separability at the 0.05 level for reflectance of different infestation levels in any of the wavelengths tested additional analysis will be pursed.

A multiple range test may be applied in addition to the ANOVA to determine if individual infestation levels are separable based on the reflectance. Further, supervised and un-supervised classification algorithms are performed on the image data. Ground truth information is used as training information for the classifications. Accuracy assessments are performed on the final classifications to determine how well the classifications were able to predict degree of insect infect infestation.

While there are a large number of bands available for analysis, these bands are often cross-correlated and are all based on the reflectance of the plant. It is rare that a combination of bands, which are inter-related, will have a significant relationship when there is no relationship found between individual bands and the dependent variable. Proceedings with multivariate analysis only after establishing that a relationship exists for the reflectance at individual bands may reduce likelihood of Type I errors. Multivariate analysis will occur using all available image bands and separately using only bands that demonstrated separability.

The second objective of this research was to determine if reflectance can be used to separate the transgenic corn varieties from the standard corn varieties. To test this objective, an analysis of variance was performed for all 128 bands of data in addition to various vegetation indices to determine if the reflectance of transgenic corn hybrid is equal to the non-transgenic corn hybrid. The test condition was corn variety and the variables were reflectance or the values for a given vegetation index. If there were no significant difference at an alpha 0.05 in all 128 bands, then it was considered that the two hybrids cannot be separated using their reflectance. However, it should be noted that there is a high likelihood of significance at the univariate level for some of the bands when separating hybrids using their reflectance.

Additional analyses, such as discriminant analysis, classification algorithms and multiple linear regression, were also performed to determine optimal bands or band combinations for delineating the two hybrids using spectral information. These analyses are conventional and well known to those skilled in the art. Coefficients of determination and classification accuracy assessments were used to determine the effectiveness of these methods.

In addition, if separability was shown, the imagery was re-sampled to lower spectral and spatial resolutions and the same test applied to determine if separability is maintained at these resolutions.

Statistical Analysis of Imagery

An analysis of variance and multiple range tests was performed on each of the reflectance bands and resulting image datasets from the index generation, classifications and other analyses to determine if separability exists between the reflectance of the corn varieties and at what level, if any, pest infestations can be separated. Multiple regression and discriminant analysis were also performed to determine the optimum bands at which separability occurs and the strength of the relationships.

Results

The above results indicate that it is possible to distinguish a transgenic plant variety from its non-transgenic near-isoline with classification accuracies as high as 98%, dependent upon location, date and hybrid variety pair. However, larger collections of hybrid varieties showed reduced classification accuracy. Separation of all transgenic from all non-transgenic varieties in the study groups achieved accuracies greater than 90% when a discriminant analysis classification was performed on a multi-temporal hyperspectral image dataset.

When separating infested corn varieties from non-infested plots of the same and different varieties of corn, very high accuracies were obtained. Second generation pest infestation was correctly identified 90-98% of the time, depending on the site for early and mid-September imagery using a simple band ratio. First generation pest infestation was classified with accuracies between 60 and 70% using the same simple ratio as that used for second generation delineation. The results indicated that identification of corn infested by European corn borer could be performed routinely using standard techniques. Accuracy varied by site, hybrid, and phenology.

Similar techniques of identifying reflectance differences between one group of plants and another group of plants can be used for distinguishing plants with differing characteristics, such as stress, traits for salt or drought tolerance, etc. For transgenic plants, markers can be introduced along with the desired genes in order to provide a ready marker for reflectance assays. Alternatively, one can compare the reflectance of a group of plants with a standard reflectance for that type of plant to determine if the group of plants is different from the standard and how the group differs from the standard.

It is to be understood that the phraseology or terminology employed herein is for the purpose of description and not of limitation. The means and materials for carrying out various disclosed functions may take a variety of alternative forms without departing from the invention.

Thus, the expressions "means to . . . " and "means for . . . " as may be found in the specification above and/or in the claims below, followed by a functional statement, are intended to define and cover whatever structural, physical, chemical, or electrical element or structures which may now or in the future exist for carrying out the recited function, whether or nor precisely equivalent to the embodiment or embodiments disclosed in the specification above. It is intended that such expressions be given their broadest interpretation.

REFERENCE

Congalton R G, "A Review of Assessing the Accuracy of Classification of Remotely Sensed Data", *Remote Sensing of the Environmental*, 37:35-46 (1991)

ENVI Staff, *ENVI User's Guide*, Better Solutions Consulting LLC., Lafayette, Colo., 614 pp (1997)

ERDAS Staff, *ERDAS Imagine Field Guide*, ERDAS, Inc., Atlanta, Ga., 656 pp. (1997)

Green et al, "A Transformation for Ordering Multispectral Data in Terms of Image Quality with Implications for Noised Removal", *IEEE Transactions on Geoscience and remote Sensing*, 26(1):65-74

Jensen J., Introductory Digital Image Processing: A remote Sensing Perspective Prentice Hall Inc., Upper Saddle River, N.J., $2^{nd}$ Edition (1996)

Mao et al, "Digital Image Processing: A Remote Sensing", Proceedings of the $15^{th}$ Biennial Workshop on Videography and Color Photography in Resource Assessment, Terre Haunte, Ind., pp. 1-12 (May 1995)

Mao C, "Hyperspectral Focal Plane Scanning—An Innovative Approach Airborne and Laboratory Pushbroom Hyperspectral Sensing", *Geospatial Information in Agriculture and Forestry*, 1:424-428 (2000)

Moran et al, "Practical Techniques for Conversion of Airborne Imagery to Reflectances", Proceedings of the $16^{th}$ Biennial Workshop on Color Photography in Resource Assessment, pp. 82-95 (1997)

Moran et al, A Refined Empirical Line Method to Calibrate Remotely Sensed Data to Reflectance, *Remote Sensing of the Environment*, 20:2653-2662 (1999)

Pearson et al, "Application of an Multispectral Digital System for Real Time Crop Condition Monitoring", Proceedings of the American Society of Photogrammetry and Remote *Sensing*, Reno, Nev. (Oct. 5-9, 1987)

Thetford et al., "Economic Potential of Landsat Thematic Mapper Data or Crop Condition Assessment of Winter Wheat", Fall Convention of the American Society of Photogrammetry and Remote Sensing, Reno, Nev. (Oct. 5-9, 1987)

GLOSSARY

Unidentified Genetic Composition referring to plant genetic composition to include trait (transgenic and non-transgenic) changes achieved from the application of traditional breeding methodology and molecular breeding methodology Reflected Solar Energy referring to energy derived from incident solar radiation reflected form a plant foliar surface(s) to a sensing device Multiband Image referring to image product(s) of a spectral sensor system for the same scene at different wavelengths Analyzing referring to the activity required to reduce a multiband image to data formats showing the differences in plant identity, pest infestation, disease, stress status, and agronomic practice first portion of the multiband image with a second portion of the multiband image, reducing at least a portion of the multiband image to a proportionate value referring to the comparison of datasets derived from one or more images to distinguish changes and interpret functional changes in the foliage Reference Value referring to the use of library values characterized by previous research to represent a parameter necessary to the correlative interpretation of an image Reference Multiband Image referring to library images derived form research to identify specific features of more recent images Physical Characteristic referring to an observable feature related to the physical definition of a scene in a multiband image Transgenic referring to the technology used to impart a desirable trait to a plant species where the trait is derived from a biological entity not related to the plant Growth Stage referring to the categorized periodic changes in plant growth and stature that have been used to specifically identify the extent of progression throughout the plant life cycle.

Fertility referring to the ability of a plant species to reproduce

Plant Species referring to an organism belonging to the plant kingdom in biological classification Stressor referring to the adverse effect a component of the plants ecology has on its growth and maturation Pest-Infestation referring to the effect of plant specific pest(s) on the growth and maturation of a plant Disease referring to the effect of plant specific diseases on the growth and maturation of a plant Soil Deficiency referring to the effect of soil nutrients and soil composition on the growth and maturation of a plant Level of Hydration referring to the effect of water availability on the growth and maturation of a plant Poisoning referring to the effect of toxicants or poisons on the growth and maturation of a plant Multiple Plants referring to a collection or large number of plants Spectral Range of the Received Multiband Image referring to the range of spectral wavelengths defining a multiband image recorded at a sensor Spatial Resolution of the Received Multiband Image.

referring to the characteristic or a multiband image that defines the magnification of a specific image

What is claimed is:

1. A method of determining a characteristic of a plant said characteristic selected from the group consisting of growth stage disease state, infestation and effects from soil deficiencies or dehydration, comprising:
    collecting reflected solar energy from a plant surface of unidentified genetic composition;
    forming the collected solar energy into a multiband image, and;
    analyzing the multiband image.

2. The method of claim 1, where analyzing the multiband image comprises at least one of comparing a first portion of the multiband image with a second portion of the multiband image, reducing at least a portion of the multiband image to a proportionate value referring to a comparison of datasets derived from at least one image and comparing the proportionate value to a reference value, and comparing at least a portion of the multiband image with a reference multiband image.

3. The method of claim 1, wherein determining a characteristic of the plant of unidentified genetic composition comprises determining a physical characteristic of the plant of unidentified genetic composition, and a physical characteristic comprises at least one of transgenic, growth stage, fertility, and plant species.

4. The method of claim 1, wherein determining a characteristic of the plant of unidentified genetic composition comprises determining a stressor of the plant of unidentified genetic composition, wherein the stressor includes at least one of a pest-infestation, disease, soil deficiency, level of hydration, and poisoning.

5. The method of claim 1, wherein a plant of unidentified genetic composition comprises multiple plants of unidentified genetic composition.

6. The method of claim 1, wherein a spectral range of the multiband image is about 400 nm to about 1000 nm.

7. The method of claim 1, wherein a spectral resolution of the multiband image is at least about 1 nm.

8. The method of claim 1, wherein a spatial resolution of the multiband image is at least about 0.5 m.

9. A method of determining a characteristic of a plant wherein said characteristic is selected from the group consisting of genetic composition, growth state, disease state, infestation and effects from soil deficiencies or dehydration, comprising:
    collecting reflected solar energy from a surface of a plant of unidentified genetic composition;
    forming the collected solar energy into a multiband image, and;
    analyzing the multiband image comprising at least one of comparing a first portion of the multiband image with a second portion of the multiband image, reducing at least a portion of the multiband image to a proportionate value referring to the comparison of datasets derived from one or more images, and comparing the proportionate value to a reference value, and comparing at least a portion of the multiband image with a reference multiband image.

10. The method of claim 9, wherein determining a characteristic of a plant of unidentified genetic composition comprises determining a physical characteristic of the plant of unidentified genetic composition, and a physical characteristic comprises at least one of transgenic, growth stage, fertility, and plant species.

11. The method of claim 9, wherein determining a characteristic of the plant of unidentified genetic composition comprises determining a stressor of the plant of unidentified genetic composition, wherein the stressor includes at least one of a pest-infestation, disease, soil deficiency, level of hydration, and poisoning.

12. The method of claim 9, wherein a plant of unidentified genetic composition comprises multiple plants of unidentified genetic composition.

13. The method of claim 9, wherein a spectral resolution of the multiband image is at least about 1 nm.

14. The method of claim 9, wherein a spatial resolution of the multiband image is at least about 0.5 m.

15. A method of determining whether a plant of unidentified genetic composition is a transgenic plant or a non-transgenic plant for plants of, comprising:
   collecting reflected solar energy from a surface of a plant of unidentified genetic composition;
   forming the collected solar energy into a multiband image, and;
   analyzing the multiband image.

16. The method of claim 15, where analyzing the multiband image comprises at least one of comparing a first portion of the multiband image with a second portion of the multiband image, reducing at least a portion of the multiband image to a proportionate value referring to comparison of datasets derived from at least one image, and comparing the proportionate value to a reference value, and comparing at least a portion of the multiband image with a reference multiband image.

17. The method of claim 15, wherein a plant of unidentified genetic composition comprises multiple plants of unidentified genetic composition.

18. The method of claim 15, wherein a spectral range of the multiband image is about 400 nm to about 1000 nm.

19. The method of claim 15, wherein a spatial resolution of the multiband image is at least about 0.5 m.

20. The method of claim 15, wherein a spatial resolution of the multiband image is at least about 0.5 m.

* * * * *